United States Patent [19]
Gustafsson et al.

[11] Patent Number: 5,779,690
[45] Date of Patent: Jul. 14, 1998

[54] DIAPER WITH OPENING IN TOP SHEET

[75] Inventors: Anders Gustafsson, Billdal; Anna Svernlöv, Kullavik; Urban Widlund, Mölnlycke, all of Sweden; Benedicte Durant, Armentières, France

[73] Assignee: Mölnlycke AB, Gothenburg, Sweden

[21] Appl. No.: 640,796

[22] PCT Filed: Dec. 8, 1994

[86] PCT No.: PCT/SE94/01179

§ 371 Date: Jul. 29, 1996

§ 102(e) Date: Jul. 29, 1996

[87] PCT Pub. No.: WO95/16419

PCT Pub. Date: Jun. 22, 1995

[30] Foreign Application Priority Data

Dec. 13, 1993 [SE] Sweden ............................ 9304132

[51] Int. Cl.⁶ .................................................. A61F 13/15
[52] U.S. Cl. ............................... 604/385.2; 604/385.1
[58] Field of Search ........................ 604/378, 385.1, 604/385.2, 386, 389, 390, 395

[56] References Cited

U.S. PATENT DOCUMENTS

| | | | |
|---|---|---|---|
| 4,662,877 | 5/1987 | Williams . | |
| 4,892,536 | 1/1990 | DesMarais et al. | 604/385.2 |
| 4,968,312 | 11/1990 | Khan | 604/385.2 |
| 4,990,147 | 2/1991 | Freeland | 604/385.2 |
| 5,062,840 | 11/1991 | Holt et al. | 604/385.1 |
| 5,624,422 | 4/1997 | Allen | 604/385.1 |

FOREIGN PATENT DOCUMENTS

| | | |
|---|---|---|
| 0 357 298 | 3/1990 | European Pat. Off. . |
| 0 486 006 | 5/1992 | European Pat. Off. . |
| 2 042 342 | 9/1980 | United Kingdom . |
| 2 174 289 | 11/1986 | United Kingdom . |

*Primary Examiner*—Mark O. Polutta
*Attorney, Agent, or Firm*—Young & Thompson

[57] ABSTRACT

A diaper having a front part (12), a back part (14) and an intermediate crotch part (13) which includes an absorbent body (1) joined to a fluid-impermeable bottom sheet (7) and a fluid-permeable top sheet (9) which lies proximal to the wearer's body in use and which includes an opening (15) situated in the back and crotch part of the diaper and elastic devices (20, 21) and which is unattached to the absorbent body at least within the region of the opening (15). Two elastic devices (20, 21) in the top sheet (9) extend divergently in relation to one another, from the front edge (16) of the opening (15) in the crotch part (13) towards the back part (14) and on respective sides of the opening in the top sheet (9).

12 Claims, 3 Drawing Sheets

5,779,690

DIAPER WITH OPENING IN TOP SHEET

CROSS-REFERENCES TO RELATED APPLICATIONS

The application is filed under 35 U. S. C. §371 as the national stage application of international application PCT/SE94/01179 filed on Dec. 8, 1994, which designated the United States of America.

FIELD OF THE INVENTION

The present invention relates to a diaper which comprises a front part, a back part and an intermediate crotch part which includes an absorbent body joined to a bottom sheet of liquid-impermeable material, and a top sheet of liquid-permeable material which lies proximal to the wearer's body in use and which contains an opening located in the back and crotch part of the diaper and elastic devices, and which is not attached to the absorbent body at least within the region of said opening.

BACKGROUND OF THE INVENTION

Diapers in which the top sheet contains an opening are known to the art from AU-A-45217/85, EP-A2-0,357,298 and EP-A2-0,486,006 and are intended to avoid irritation of the skin as a result of excrement, e.g. faeces, coming into contact with the wearer's skin. According to these publications, this is achieved because as the elastic devices present provided in the top sheet contract, the absorbent body is deformed into a basin-like configuration while, at the same time, the top sheet is distanced from the bottom of the basin and forms a basin lid or cove which includes said opening. One problem with diapers of this kind is that the opening formed in the top sheet must be sufficiently large and sufficiently well situated as to ensure that excrement discharged by the wearer will fall down onto the absorbent body. There is a serious danger that any excrement which falls on the top sheet will leak from the diaper and irritate the wearer's skin.

SUMMARY OF THE INVENTION

The object of the present invention is to reduce the risk of excrement being deposited on one side of the opening in the top sheet to a greater extent than has hitherto been achieved.

This is achieved in accordance with the invention with a diaper of the kind defined in the introduction which is characterized in that two elastic devices extend divergently in relation to one another, from the front edge of the opening in the crotch part towards the back part and on both sides of the opening in the top sheet. This ensures that the side edges of the opening will be held apart reliably while the diaper is worn, so as to retain the intended width of the opening.

According to one preferred embodiment of the invention, two elastic devices extend divergently in relation to one another from the front edge of the opening in the crotch part to the front part of the diaper, and the elastic devices which extend divergently rearwards from the opening extend along the side edges of the opening. Furthermore, the elastic devices in the top sheet extend in the longitudinal direction of the diaper essentially from the forward diaper attachment of the top sheet essentially to the rear diaper attachment of said top sheet, and the two elastic devices that extend along the side edges of the opening continue to the front part of said diaper. The transverse distance between the side edges of the opening in the top sheet is preferably 3–6 cm at the excretion point. The absorbent body includes a main body of hourglass configuration and two side-bodies which are positioned laterally outside the main body on respective sides thereof and in the curved region of said main body and are enclosed between the bottom sheet and an inner fluid-permeable casing sheet.

BRIEF DESCRIPTION OF THE DRAWINGS

The invention will now be described in more detail with reference to the accompanying drawings, in which.

DESCRIPTION OF THE PREFERRED EMBODIMENTS

Figure 1:
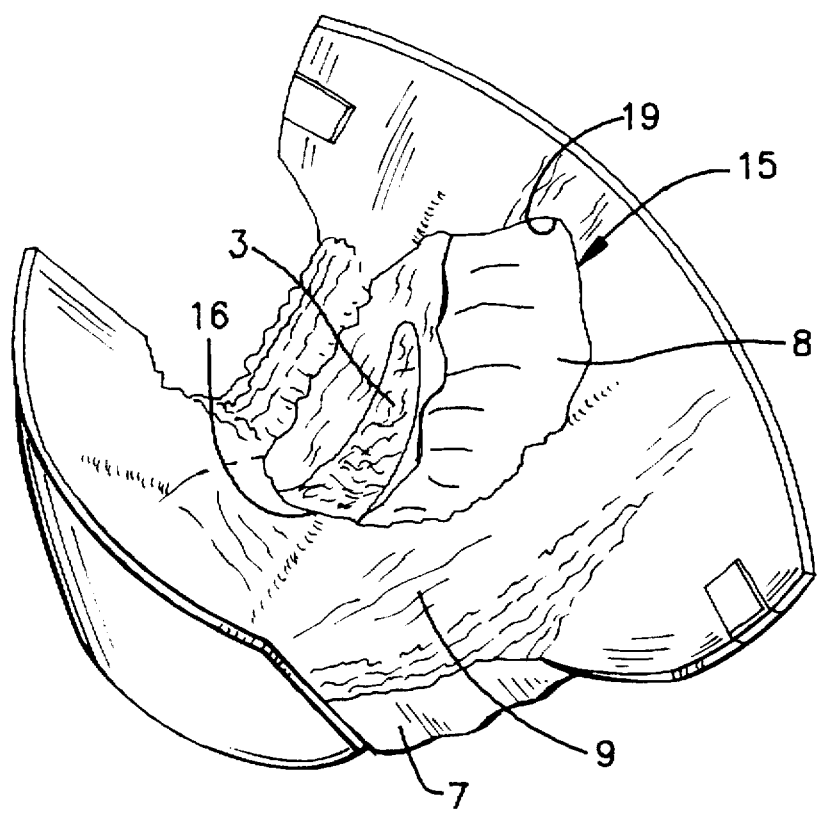
FIG. 1 is a schematic, perspective view seen obliquely from above of a first embodiment of an inventive diaper.

The diaper illustrated in FIGS. 1–4 includes an absorbent body unit 1 which is comprised of a main body 2 of hourglass configuration and two side bodies 3, 4. The main body 2 is comprised of two layers 5, 6 of which the upper layer 5, and also the side-bodies 3, 4, are comprised of air-laid cellulose fluff, whereas the bottom layer 6 includes an absorbent reel material of the kind described in Swedish Patent Application No. 9203445-3, which contains a dry formed sheet containing 5–100% cellulose fibres having a bulk density of between 0.2–1.0 g/cm$^3$ and a surface weight of between 30–2000 g/m$^2$ and which is formed by compressing a web containing cellulose fibres without subsequent defibration and fluff forming. The reader is referred to the above-mentioned application for closer details of such reel material. As will be seen from FIG. 4, the layer 6 is rectangular in shape and extends only beneath part of the layer 5.

The absorption body unit 1 is enclosed between an outer casing sheet or backing sheet 7 of liquid-impermeable material, such as polyethylene plastic for instance, and an inner liquid-permeable casing sheet 8, which is preferably comprised of nonwoven material. The inner sheet 8 and the backing sheet 7 are preferably of identical shape and are joined together at parts which lie outside the absorbent body 1. As will best be seen from FIG. 4, the side-bodies 3, 4 are positioned laterally slightly outside the main body 2 and the casing sheets 7, 8 are mutually joined in the gaps between the main body and the side bodies.

Figure 2:
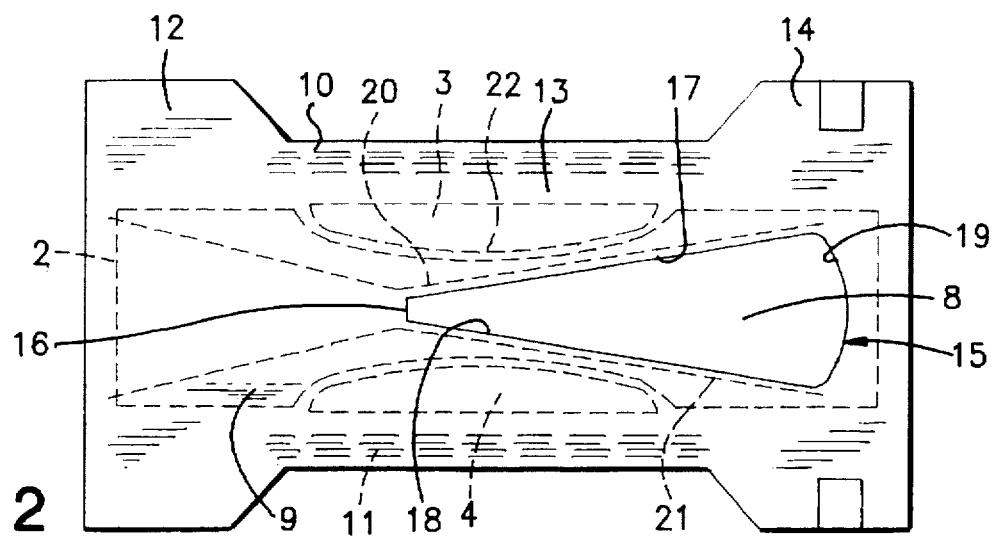
FIG. 2 is a schematic view from above of the diaper in FIG. 1 with the diaper shown in a flat state.
Figure 3:
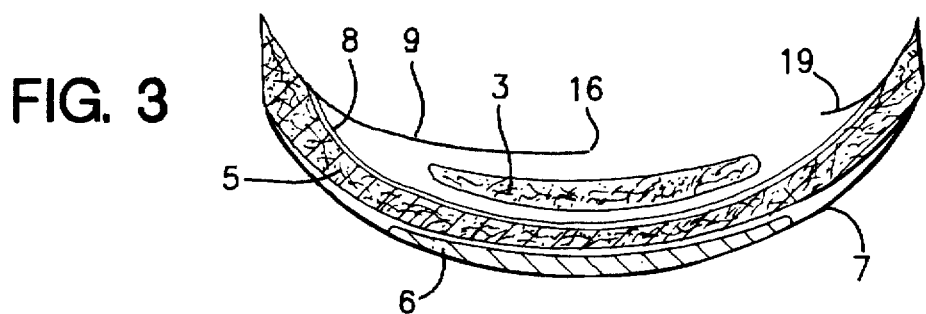
FIG. 3 is a schematic cross-sectional view of the diaper shown in FIG. 1.
Figure 4:
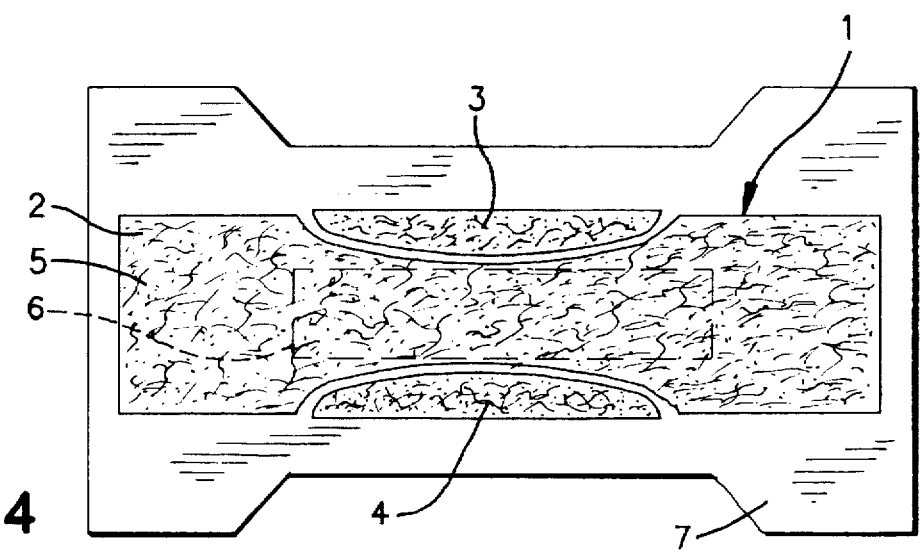
FIG. 4 is a view corresponding to the view in FIG. 2 of the bottom sheet and the absorbent body of the diaper shown in FIG. 1.

The diaper also includes a top sheet 9 whose shape is identical to the shapes of the casing sheets 7, 8 and which is fastened to said sheets along diaper edge parts, so that the top sheet will be generally free from the absorbent body 1, i.e. generally unattached thereto. As illustrated in FIGS. 1 and 2, the diaper includes leg elastic in the form of elastic devices 10, 11 which extend along the side edges of the crotch part 13 and along parts of the front diaper part 12 and the back diaper part 14. In the illustrated embodiment, the elastic devices are comprised of four elastic threads which are attached in a stretched state between the top sheet 9 and the inner casing sheet 8 and fastened to said sheets. It will be understood that the number of leg elastics used may be greater or fewer than four threads, and that other types of elastic devices may be used, such as elastic bands or ribbons, bands of film material that has elastic properties, etc. It will also be understood that the elastic devices 10, 11 may be mounted between the bottom sheet 7 and the inner casing sheet 8 instead.

An opening 15 is formed in the top sheet 9 symmetrically in relation to the longitudinal direction of the diaper. The front edge 16 of this opening is located between the wetting point and the excretion point. By wetting point, it is meant that region of the diaper within which urine discharged by the wearer is expected to be deposited when the diaper is correctly positioned on the wearer, and by excretion point is meant correspondingly that region of the diaper within which, faeces will be deposited on a correctly positioned diaper, i.e. those regions which lie opposite to the external urethra orifice and the anus of the wearer, while taking into consideration normal variations in the wearer's anatomy within the size ranges of the wearer for which the used diaper is dimensioned. The side edges 17, 18 of the opening 15 extend divergently away from one another in a direction towards the back diaper part, and the rear edge 19 of the opening is arcuate in shape and located in the back diaper part at a short distance from the rear end of the absorbent body.

Two elastic threads 20, 21 are fastened in a stretched state to the top sheet 9 and extend from the forward part of the front diaper part 12 to the rear part of the back diaper part 14. The threads 20, 21 extend mutually convergent from the front part 12 to the forward edge 16 of the opening 15 and then extend along the side edges 17, 18 of the opening to points generally abreast of the rear edge 19 of the opening. In the illustrated embodiment, the threads 20, 21 are mounted between the top sheet and narrow strips of nonwoven material (not shown) which are fastened to the threads and the top sheet with the aid of glue or by some other suitable means. In the illustrated embodiment, the strips are disposed along the full length of the threads and are thus fastened to the top sheet along the whole of its length. This is not absolutely necessary, however, since the desired function can be achieved sufficiently well when the threads are fastened to the ton sheet at their respective ends and on both sides of the front edge.

In one variant of the invention, the nonwoven strips are fastened to the top sheet at their respective edges so as to form guide passages for elastic threads extending therethrough. In the case of this embodiment, it is sufficient to fasten the threads to the top sheet at the ends of the passages. For instance, if the nonwoven strips extend along the full length of the elastic threads it is sufficient to fasten the ends of the threads to the top sheet. It is preferred that the threads will extend freely in the guide passages, at least along the edges of the opening 15. When the top sheet lacks the provision of guide passages forwardly of the opening 15, the nonwoven strips can be formed unitary with the top sheet, by folding said top sheet in conjunction with cutting out the opening 15. In this case, the provision of separate nonwoven strips in front of the opening can be omitted, in which case the threads will lie freely between their forward top sheet attachment points and the ends of the passages at the forward edge of the opening. As will be understood, it is also possible to fasten the threads to the top sheet along the whole of that part thereof which extends in front of the opening, for instance by attaching separate nonwoven strips.

FIG. 2 illustrates the diaper in a flat state, i.e. the state in which the diaper is found during manufacture, in which the diaper is held stretched against the action of the spring force exerted by the elastic devices. When the finished diaper is released from its stretched state, the elastic devices 10, 11, 20 and 21 strive to contract to a tensionless or relaxed state, therewith deforming the diaper to the shape illustrated in FIGS. 1 and 3.

Contraction of the elastic threads 20, 21 causes the top sheet to gather together and therewith shorten. In order to allow this shortening of the top sheet to take place, the main body 2 of the absorbent body unit 1 is curved at the same time as the side bodies 3, 4 are swung upwards about hinge means formed by the casing sheets 7, 8, these sheets being joined in the gaps defined between respective side bodies 3, 4 and the main body 2. Thus, the elastic threads 20, 21 are instrumental in maintaining the top sheet 9 in spaced relationship with the absorbent body 1.

It is mentioned in this respect that FIG. 1 illustrates the diaper when no load is exerted thereon, and thus not when the diaper is worn. As will be understood, the shape adopted by a diaper when in use will depend on the anatomy of the wearer, and the diaper is so dimensioned that the elastic threads 20, 21 will normally be stretched slightly as the diaper is placed in position on the wearer. However, the length of the diaper is such that a large part of the fold or gather in the top sheet will remain after having put on the diaper, so that the absorbent body will be located at a distance from the top sheet along a greater part of its extension, even after having put the diaper on.

Thus, there is found between the absorbent body and the top sheet a space in which excrement i.e. faeces is kept out of contact with the skin. Furthermore, it must be ensured that excrement is deposited in this space and not on the top sheet, and it will therefore be understood that the size and positioning of the opening are of decisive importance, particularly with regard to the excrement point. It has been found that the distance between the side edges 17, 18 of the opening should be at least 3 cm at the excrement point, and that the front edge of the opening 15 should lie at least 1 cm and preferably 2 cm forwardly of the front edge 16, and that the front edge 16 should be at leas. 2 cm long. Because the elastic threads 20, 21 exert a spring force in both the longitudinal and transverse directions of the diaper when the diaper is worn, the front edge of the opening 15 and its side edges 17, 18 will be stretched outwardly sc as to ensure that the aforesaid distances are retained when the diaper is in use. In order to achieve a high outward tensioning effect, the ends of the threads 20, 21 will preferably lie on the same level as the side edges of the absorbent body 1 essentially in a lateral direction.

In addition to gathering together the top sheet 9, the elastic threads 20, 21 also have a sealing function by lying sealingly against the wearer's body when the diaper is worn. This greatly reduces the risk of discharged urine running along the top sheet instead of passing through said sheet and being absorbed by the absorbent body in the manner intended. The fact that the elastic threads extend along the side edges of the opening also greatly reduce the risk of the position of the opening 15 being changed as a result of external forces on the diaper, for instance as the wearer of the diaper moves. An added advantage is that when the absorbent body is subjected to an external load and subsequently pressed towards the body of the wearer, it is more difficult for excrement to seep over the edges of the opening 15 and onto the top sheet 9. In order to obtain these sealing functions, it has been found that the distance between the side edges 17, 18 of the opening 15 at the centre of the excrement point should not exceed 6 cm and will preferably be smaller than 5 cm. The length of the front edge 16 of the opening 15 will preferably not exceed 4 cm.

From the aspect of absorption, the side bodies 3, 4 are not joined to the remainder of the absorbent body 1 and form safety bodies which absorb fluid when the main body 2 becomes saturated or is unable to absorb discharged fluid for some reason or another. In addition to this function, the side bodies also contribute to the stability of the basin that is formed when the top sheet is gathered together and prevent the main absorbent body in its entirety coming into abutment with the wearer's body when the diaper is subjected to an external load.

Figure 5:
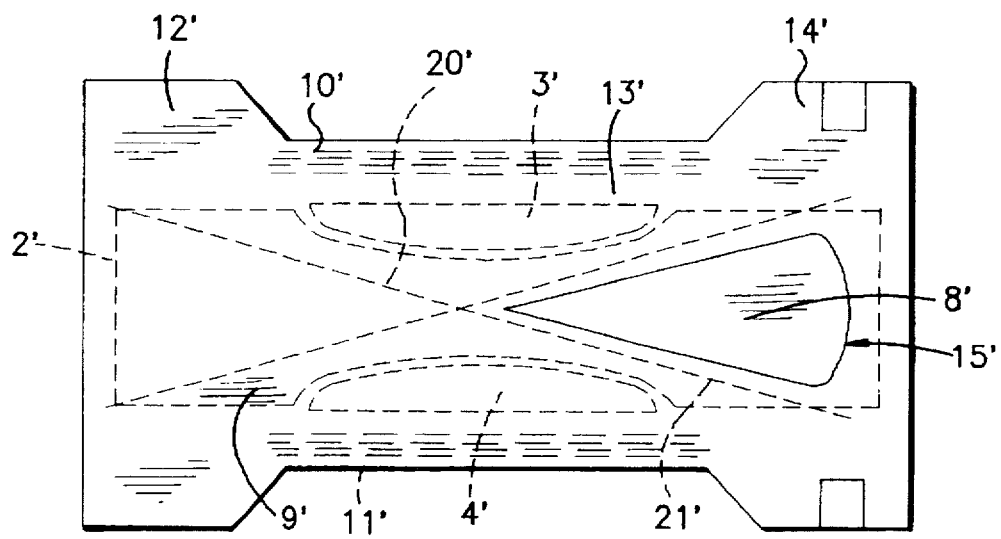
FIG. 5 is a view corresponding to the view of FIG. 2 and illustrates a second embodiment of an inventive diaper.

FIG. 5 illustrates a second embodiment of an inventive diaper in a view corresponding to the view of FIG. 2. Diaper components corresponding to the FIG. 2 embodiment have been identified with the same reference signs to which a prime has been added. In the case of the diaper illustrated in FIG. 5, the elastic threads 20', 21' cross one another in front of the opening 15' in the top sheet 9', and the opening is terminated forwardly in a point. The opening 15' thus has a punctiform front edge. In other respects, the diaper illustrated in FIG. 5 has the same construction as the diaper illustrated in FIGS. 1-4.

An extremely good sealing function can be achieved by the top sheet 9' as a result of the mutually crossing threads 20', 21'. The point of intersection of the elastic threads 20', 21' shall lie between the wetting point and the excrement point and the same requirements as those placed on the diaper according to FIG. 1-4 with regard to the distance between the side edges of the opening 15 at the excrement point also apply to the opening 15'. Accordingly, the point of intersection will lie relatively close to the wetting point, meaning that the illustrated embodiment cannot be worn readily by males, since space must be found between the elastic threads 20', 21' to accommodate the scrotum. Naturally, it is possible within the scope of the present invention to modify the extension of the threads within the region of the wetting point so as to prepare room for the scrotum.

The embodiment illustrated in FIG. 5 is highly advantageous from the aspect of manufacture, since the threads can be laid out easier than with the diaper according to the embodiment illustrated in FIGS. 1-4. For this reason, it may sometimes be justified to use intersecting elastic threads at an opening in the top sheet of the embodiment illustrated in FIGS. 1-4, even though the intersection point of the threads would then lie in or forwardly of the wetting point and despite the fact that this would impair the sealing function of the threads in the forward part of the diaper crotch part. It should be mentioned in this regard that it is possible to permit the side edges of the opening, and therewith the threads that diverge towards the back part, to extend at a greater angle in relation to one another, so as to increase the distance between the threads and the side edges at the excrement point.

Figure 6:
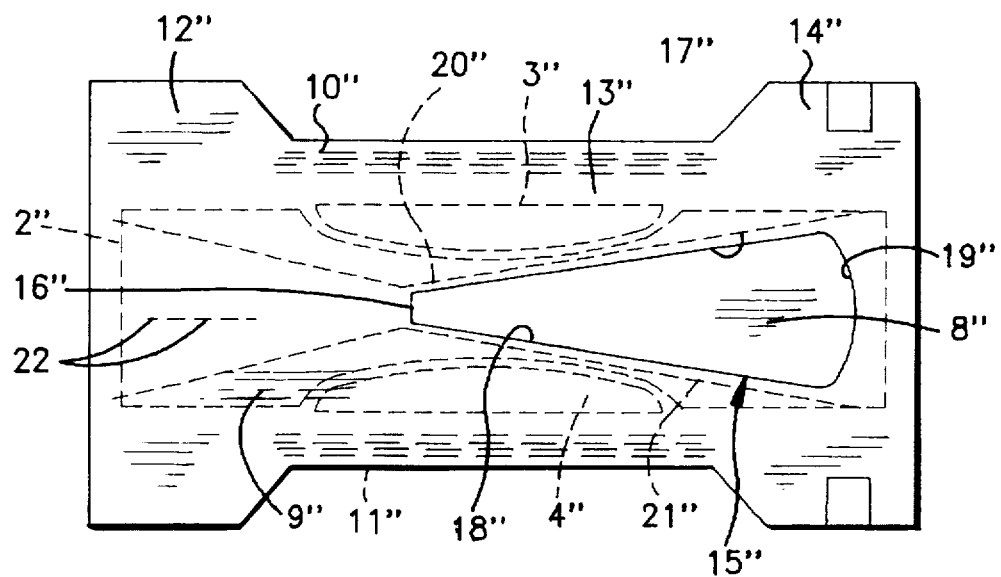
FIGS. 6 and 7 are views corresponding to respective views of FIGS. 2 and 3 and illustrate a third embodiment of an inventive diaper.
Figure 7:
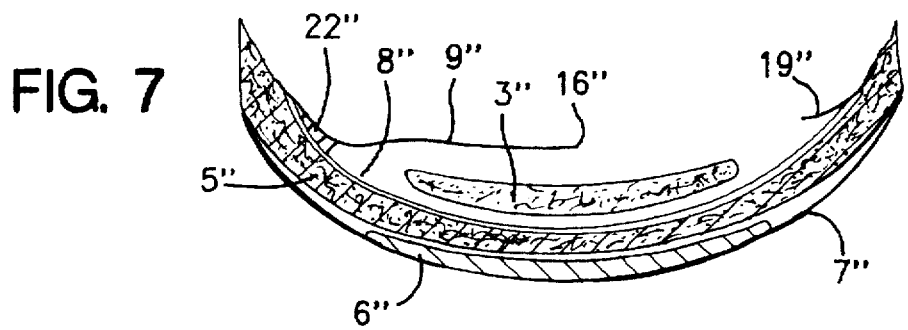

FIGS. 6 and 7 illustrate a third embodiment of an inventive diaper. The diaper components shown in these Figures have been identified with the same reference signs as those used in FIGS. 2 and 3 respectively, with the addition of a double prime.

The embodiment illustrated in FIGS. 6 and 7 differs from the embodiment illustrated in FIGS. 1-4 in that the top sheet 9" is joined to the inner casing sheet 8" by a number of discrete attachment points 22 disposed along the longitudinal symmetry axis of the diaper. This provides greater contact between the top sheet and the underlying absorbent body within the urine receiving part of the diaper. However, this attachment region must not be allowed to extend too close to the front edge 16" of the opening 15", since otherwise the distance between the top sheet 9" and the absorbent body 2" will be too small at the front edge 16" when the top sheet is gathered together as it passes from a flat to a curved state. It has been found that this distance should be greater than 2 cm, preferably greater than 3 cm. It will be understood that the top sheet can be fastened to the inner casing sheet in some way other than through the medium of discrete attachment points 22, for instance by applying a continuous glue bead instead of discrete glue patches, or by linear welding instead of spot welding. However, the attachment region will preferably have only a small lateral extension, so as not to affect curving of the absorbent body to any great extent.

It will be understood that the described and illustrated embodiments of the invention can be modified without departing from the scope of the present invention. For instance, the shape and dimensions of the opening can be changed, particularly the rear part of the opening outside the excrement point. Furthermore, the elastic threads in the front part of the top sheet need not be an extension of the threads extending along the side edges of the opening, but may have the form of separate elements and may optionally be omitted in those embodiments in which the side edges of the opening converge to a point. However, it is preferred that shortening of the top sheet as a result of contraction of the elastic threads in the longitudinal direction is distributed over the whole of the top sheet, among other things so as to appropriately tension the elastic threads, and consequently an embodiment in which no elastic threads are found in front of the opening is not to be preferred. It is also preferred that the elastic threads extend longitudinally generally from the forward top sheet attachment in the diaper to the rear top sheet attachment. Naturally, the elastic in the top sheet may be comprised of other elastic devices than single elastic threads, and may for instance have the form of elastic tapes, bands or a plurality of mutually parallel threads. The invention can also be applied to diapers of another configuration than the configuration of the illustrated diapers, for instance the absorbent body may be constructed differently. It should be mentioned in this regard that the term "diaper" as used in the present document is intended to include so-called pants-type diapers or "training pants" and incontinence guards for people who are afflicted with double incontinence. The invention is therefore restricted solely by the content of the following claims.

We claims:

1. A diaper extending in a longitudinal direction and comprising:
    a front part, a back part, and an intermediate crotch part, an absorbent body joined to a fluid-impermeable bottom sheet, and a fluid-permeable top sheet which lies proximal to a wearer's body in use, said top sheet including an opening situated in the back and crotch parts of the diaper and elastic devices, said top sheet being unattached to the absorbent body at least within the region of the opening, and wherein two elastic devices in the top sheet extend divergently in relation to one another, from a front edge of the opening in the crotch part towards the back part and on respective sides of the opening in the top sheet.

2. A diaper according to claim 1, wherein the two diverging elastic devices in the top sheet extend along side edges of the opening.

3. A diaper according to claim 2, wherein the two elastic devices that extend along the side edges of the opening extend further to the front part of the diaper and intersect one another at a point in the crotch part that lies in front of the front edge of the opening.

4. A diaper according to claim 1, wherein the two elastic devices in the top sheet extend in the longitudinal direction of the diaper essentially from a forward attachment of the top sheet in the diaper generally to a rear attachment of the top sheet in said diaper.

5. A diaper according to claim 1, wherein the two elastic devices in the top sheet extend divergently in relation to one from the front edge of the opening in the crotch part to the front part.

6. A diaper according to claim 2, wherein the front edge of the opening is located between a wetting point and an excrement point, and the transversal distance between the side edges of the top sheet opening at said excrement point is 3–6 cm.

7. A diaper according to claim 1, wherein the absorbent body includes a main body of hourglass configuration and two side bodies which are placed laterally outside the main body on respective sides thereof, and in a curved region of said main body.

8. A diaper according to claim 7, wherein the absorbent body is enclosed between the bottom sheet and a fluid-permeable inner casing sheet (8).

9. A diaper according to claim 1, wherein the two elastic devices in the top sheet are fastened to the top sheet along the whole of its length.

10. A diaper according to claim 1, wherein the two elastic devices are fastened to the top sheet solely at their respective ends and immediately in front of the front edge of the opening.

11. A diaper according to claim 1, wherein the top sheet is fastened to remaining parts of the diaper along the whole of its front and rear edge.

12. A diaper according to claim 8, wherein the top sheet is joined to the inner casing sheet surrounding the main body in a central longitudinal extending attachment region which extends from a forward attachment of the top sheet to a point which is distanced from the front edge of the opening, said distance being greater than 2 cm in a non-gathered state of the top sheet.

\* \* \* \* \*